US00PP10508P

United States Patent [19]

Stahnke et al.

[11] Patent Number: Plant 10,508

[45] Date of Patent: Jul. 21, 1998

[54] AZALEA PLANT NAMED 'OSTALETT'

[76] Inventors: Otto Stahnke; Peter Dettmer; Eleonore Dettmer, all of Bromer Strasse 104, 38524 Sassenburg-Grussendorf, Germany

[21] Appl. No.: 802,577

[22] Filed: Feb. 19, 1997

[51] Int. Cl.[6] ..... A01H 5/00

[52] U.S. Cl. ..... Plt./56

[58] Field of Search ..... Plt./56

*Primary Examiner*—Elizabeth C. Kemmerer

*Attorney, Agent, or Firm*—C. A. Whealy

[57] ABSTRACT

A new and distinct cultivar of Azalea plant named 'Ostalett', characterized by its uniform and freely branching plant habit; durable, very dark green, glossy leaves; atteactive semi-double, dark purple-colored flowers with dark crimson-speckled centers; and exception postproduction longevity.

2 Drawing Sheets

SUMMARY OF THE INVENTION

The present invention relates to a new and distinct cultivar of Azalea, botanically known as *Rhododendron simsii*, and hereinafter referred to by the cultivar name Ostalett.

The new cultivar is a product of a planned breeding program conducted by the inventors in Sassenburg-Grussendorf, Germany. The objective of the breeding program is to create new Azalea cultivars that are durable and have inflorescences with desirable flower colors and uniform plant habit. The new cultivar originated from a cross made by the inventors of the commercial cultivar Adonia (not patented) as the male, or pollen, parent with an unnamed proprietary seedling selection as the female, or seed, parent. The cultivar Ostalett was discovered and selected by the inventors as a flowering plant within the progeny of the stated cross in a controlled environment in Sassenburg-Grussendorf, Germany.

Compared to plants of the male parent, the cultivar Adonia, plants of the new Azalea have darker and glossier leaves, more intense flower color, significantly longer postproduction longevity, and are less susceptible to diseases. Compared to plants of the female parent, a proprietary seedling selection with violet-colored flowers, plants of the new Azalea have a more uniform plant habit, more durable foliage, and flower earlier.

Asexual reproduction of the new cultivar by terminal cuttings taken at Sassenburg-Grussendorf, Germany, has shown that the unique features of this new Azalea plant are stable and reproduced true to type in successive generations of asexual reproduction.

The following traits have been repeatedly observed and are determined to be the unique characteristics of 'Ostalett'. These characteristics in combination distinguish the new Azalea plant as a new and distinct cultivar:

1. Uniform plant habit.
2. Very freely branching.
3. Durable, very dark green, glossy leaves.
4. Attractive semi-double, dark purple-colored flowers with dark crimson-speckled centers.
5. Exception postproduction longevity with plants maintaining flowers for about six weeks.

Plants of the new Azalea can be compared to plants of the cultivar Dr. Heursel (not patented). However in side-by-side comparisons in Sassenburg-Grussendorf, Germany, under commercial practice, plants of the new Azalea have a more compact growth habit, darker green and glossier foliage, more intense purple flower color, and larger flowers than plants of the cultivar Dr. Heursel.

The new Azalea plant has not been observed under all possible environmental conditions. The phenotype may vary significantly with variations in environment such as temperataure, light level, nutrition and water status without, however, any variance in genotype.

BRIEF DESCRIPTION OF THE DRAWINGS

The accompanying colored photographs illustrate the overall appearance of the new cultivar, showing the colors as true as it is reasonably possible to obtain in colored reproductions of this type.

The first photograph comprises a side perspective view of typical plant of 'Ostalett'.

The second photograph comprises a close-up view of a typical flowers of 'Ostalett'. Flower and foliage colors in the photographs may appear different from the actual colors due to light reflectance.

DETAILED DESCRIPTION OF THE INVENTION

The following observations, measurements, values, and comparisions describe plants grown in Salinas, Calif., in 12.5-cm containers under glass with day temperatures ranging from 24° to 27° C., night temperatures ranging from 13° to 16° C., and light levels averaging 4,500 footcandles.

In the following description, color references are made to The Royal Horticultural Society Colour Chart except where general terms of ordinary dictionary significance are used.

Classification:

*Botanical.*—*Rhododendron simsii* cv. Ostalett.

Parentage:

*Male or pollen parent.*—*Rhododendron simsii* cv. Adonia (not patented).

*Female or seed parent.*—Unnamed proprietary *Rhododendron simsii* seedling section with violet-colored flowers.

Propagation:

*Type.*—By terminal cuttings.

*Time to initiate roots.*—About 23 days at temperatures of 22° C.

*Rooting habit.*—Strong roots, vigorous and finely-branched.

Plant description:

*Plant form and growth habit.*—Perennial, evergreen, upright to outwardly spreading, inverted triangle. Moderate vigor.

*Branching habit.*—Dense, very freely branching, about five lateral branches develop after removal of terminal apex.

*Plant height, soil level to top of flowers.*—About 15 cm.

*Plant diameter, area of spread.*—About 27 cm.

*Lateral branch description.*—Length: About 10 cm. Diameter: About 4 mm. Color: Immature: 147C. Mature: 166B. Texture: Pubescent.

Foliage description:

*Arrangement.*—Alternate, single.

*Leaf size, largest leaves.*—Length: About 4 cm. Width: About 2.5 cm.

*Leaf shape.*—Elliptic to ovate.

*Leaf apex.*—Acute.

*Leaf base.*—Cuneate.

*Margin type.*—Entire.

*Texture.*—Durable, leathery, very glossy, both surfaces pubescent.

*Color.*—Young foliage, abaxial surface: 147A. Young foliage, adaxial surface: 147B. Mature foliage, abaxial surface: Darker than 147A. Mature foliage, adaxial surface: 147B.

*Petiole.*—Length: About 8 mm. Diameter: About 2 mm. Color: 144 A.

Flower description:

*Natural flowering season.*—Spring after sufficient cool period.

*Flower arrangement.*—Flowers arranged singly at terminals with usually three to five flowers per terminal. Flowers face upward and outward. Freely flowering.

*Flower appearance.*—Star-shaped semi-double. Dark purple-colored petals with dark crimson-speckled centers. Flowers persistent.

*Flower diameter.*—About 8 cm.

*Flower longevity.*—Seven to nine days depending on temperature.

*Flower bud.*—Rate of opening: About three days depending on temperatures. Length: About 2.3 cm. Diameter: About 1 cm. Shape: Ovoid. Color: 78A.

*Petals.*—Appearance: Satiny, smooth. Texture: Glabrous. Arranement: Semi-double. Outer corolla consists of five fused petals and inner corolla consists of up to 5 irregularly-shaped fused stamenoidal petaloids. Shape: Rounded to ovate with rounded apex. Margin: Entire, undulating giving a slightly ruffled appearance. Size: Length: About 5 cm. Width: About 3.7 cm. Color: When opening, abaxial surface: 78A with speckles, 59A, at base. When opening, adaxial surface: 78A fading to 78B at base. Fully opened, abaxial surface: 78A with speckles, 59A, at base. Over time, petal color darkens to 72A. Fully opened, adaxial surface: 78A.

*Sepals.*—Appearance: Five sepals fused into a star-shaped calyx. Texture: Pubescent. Shape: Elliptic. Apex: Rounded. Margin: Entire. Color, abaxial and adaxial surfaces: 144A.

*Peduncles.*—Length: About 1.5 cm. Angle: Upright. Strength: Rigid. Color: 59A.

*Reproductive organs.*—Androecium: Stamen number: Five, usually fused into petaloids. Anther shape: Oblong. Anther size: About 1 mm. Anther color: Dark purple. Amount of pollen: Little to none. Gynoecium: Pistil number: One. Pistil length: About 3.5 cm. Stigma shape: Rounded. Stigma color: Dark Pink, 63A. Style length: About 3 cm. Style color: 63A. Ovar color: Green.

Disease resistance: No known Azalea diseases observed to date on plants grown under commercial greenhouse conditions. Plants of the new Azalea appear to be less susceptible to diseases than other commercial cultivars.

Seed production: Seed production has not been observed.

It is claimed:

1. A new and distinct Azalea plant named 'Ostalett', as illustrated and described.

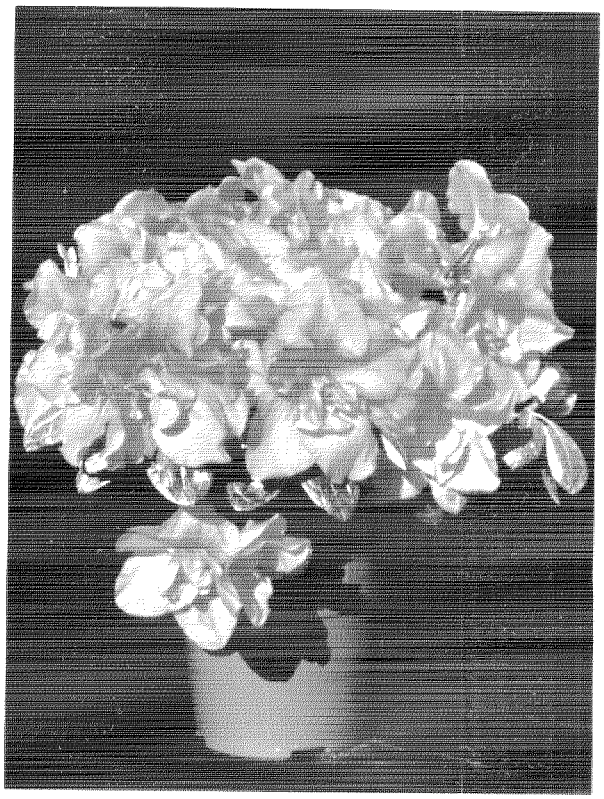

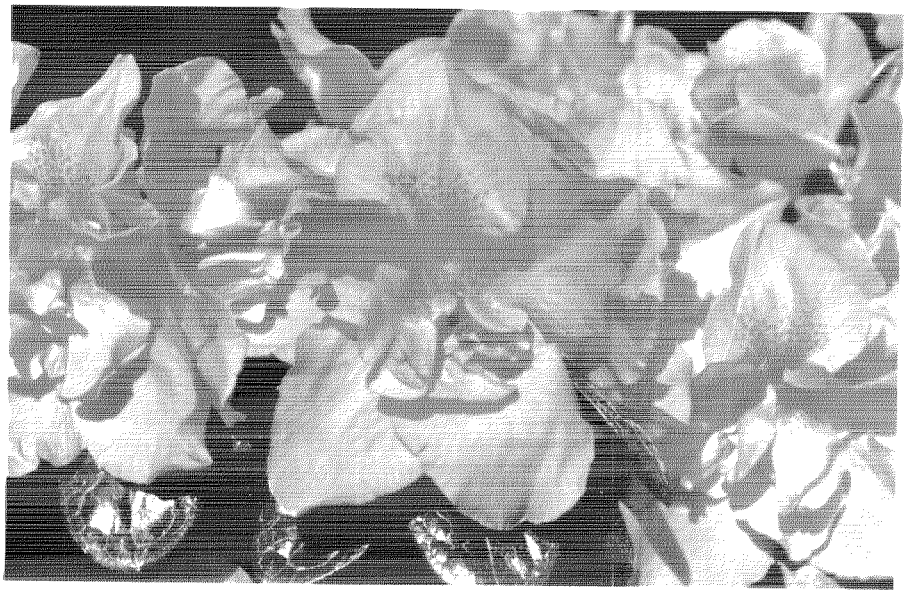

* * * * *